(12) United States Patent
Sonnenberg et al.

(10) Patent No.: US 7,384,535 B2
(45) Date of Patent: Jun. 10, 2008

(54) BATH ANALYSIS

(75) Inventors: Wade Sonnenberg, Edgartown, MA (US); Leon R. Barstad, Raynham, MA (US); Raymond Cruz, Watertown, MA (US); Gary Hamm, Medford, MA (US); Mark J. Kapeckas, Marlborough, MA (US); Erik Reddington, Ashland, MA (US); Katie Price, Stoneham, MA (US); Thomas Buckley, Rocky Hill, CT (US); Trevor Goodrich, Windsor, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 756 days.

(21) Appl. No.: 10/831,726

(22) Filed: Apr. 24, 2004

(65) Prior Publication Data

US 2005/0016856 A1   Jan. 27, 2005

Related U.S. Application Data

(60) Provisional application No. 60/465,297, filed on Apr. 25, 2003.

(51) Int. Cl.
*G01N 27/42* (2006.01)
(52) U.S. Cl. .................. 205/775; 205/81; 205/787; 204/434
(58) Field of Classification Search ............... 205/775, 205/780.5, 786.5, 787, 791, 81; 204/434
See application file for complete search history.

(56) References Cited

U.S. PATENT DOCUMENTS

| 4,038,161 A | 7/1977 | Eckles et al. |
|---|---|---|
| 4,132,605 A | 1/1979 | Tench et al. |
| 4,666,567 A | 5/1987 | Loch |
| 4,917,774 A | 4/1990 | Fisher |
| 4,917,777 A | 4/1990 | Fisher |
| 5,004,525 A | 4/1991 | Bernards et al. |
| 5,192,403 A | 3/1993 | Chang et al. |
| 5,223,118 A | 6/1993 | Sonnenberg et al. |
| 5,252,196 A | 10/1993 | Sonnenberg et al. |
| 5,972,192 A | 10/1999 | Dubin et al. |
| 6,365,033 B1 | 4/2002 | Graham et al. |
| 6,471,845 B1 | 10/2002 | Dukovic et al. |

(Continued)

FOREIGN PATENT DOCUMENTS

DE   199 11 447 A1   3/1999

(Continued)

OTHER PUBLICATIONS

Tench et al., "Cyclic Pulse Voltammetric Stripping Analysis of Acid Copper Plating Baths"; J. Electrochem. Soc.: Electrochemical Science and Technology; Apr. 1985; pp. 831-834.

(Continued)

*Primary Examiner*—Kaj K. Olsen
(74) *Attorney, Agent, or Firm*—John J. Piskorski

(57) ABSTRACT

Analytical methods are disclosed for determining the quantity of brightener and leveler in an electroplating bath in the presence of other organic additives, such as accelerators, brighteners and suppressors. The methods improve the reproducibility of measuring brighteners and levelers in electroplating baths.

8 Claims, 2 Drawing Sheets

U.S. PATENT DOCUMENTS

| | | |
|---|---|---|
| 6,508,924 B1 | 1/2003 | Gomez et al. |
| 6,551,479 B1 | 4/2003 | Graham et al. |
| 6,572,753 B2 * | 6/2003 | Chalyt et al. .................. 205/81 |
| 6,592,747 B2 * | 7/2003 | Horkans et al. ............. 205/775 |
| 6,673,226 B1 * | 1/2004 | Kogan et al. ................. 205/81 |
| 6,709,568 B2 * | 3/2004 | Han et al. ..................... 205/81 |
| 6,808,611 B2 * | 10/2004 | Sun et al. ................... 205/787 |
| 6,827,839 B2 | 12/2004 | Sonnenberg et al. |
| 6,936,157 B2 * | 8/2005 | Robertson ................... 205/775 |
| 2006/0151327 A1 * | 7/2006 | Sonnenberg et al. .......... 205/81 |

FOREIGN PATENT DOCUMENTS

| | | |
|---|---|---|
| EP | 0 597 474 A1 | 5/1994 |
| EP | 0 785 297 B1 | 1/2000 |
| WO | WO 99/57549 | 11/1999 |

OTHER PUBLICATIONS

Haak et al., "Cyclic Voltammetric Stripping Analysis of Acid Copper Sulfate Plating Baths"; Plating and Surface Finishing; Mar. 1982; pp. 62-66.

* cited by examiner

BATH ANALYSIS

This application claims the benefit of U.S. Provisional Application(s) No(s).: 60/465,297 filing date Apr. 25, 2003.

BACKGROUND OF THE INVENTION

The present invention is directed to a method of analyzing organic additives in electroplating baths. More specifically, the present invention is directed to a method of analyzing organic additives in electroplating baths having improved reproducibility.

Electroplating baths for copper and other metals are typically aqueous, or mostly aqueous, solutions composed of metal compounds or salts, ionic electrolytes, and various additives such as brighteners, suppressors, levelers, accelerators, surfactants, and defoamers. These electroplating baths, which are used to deposit metals or semimetals such as copper, nickel, gold, palladium, platinum, ruthenium, rhodium, tin, zinc, antimony, or alloys such as copper-tin (brass), copper-zinc (bronze), tin-lead, nickel-tungsten, and cobalt-tungsten-phosphide are used in applications such as the fabrication of electronic devices and components, such as conductive circuits for printed circuit boards, multichip modules, and semiconductor devices.

Reliable operation of these electroplating baths in a manufacturing process requires that methods of analysis are employed to determine the appropriate concentrations of the reagent species for bath startup. These analytical methods also are used to determine the concentrations of species in the bath during operation, often with on-line feedback control, to allow the components of the bath to be monitored and adjusted as required to maintain concentrations within pre-determined limits. Bath analytical methods also are used to determine the chemical identity and concentrations of species that are produced in the bath as a consequence of chemical and electrochemical reactions that take place during bath operation and/or idling.

Electrochemical methods are used principally for the analysis of acid copper plating baths used for plating circuitry on printed wiring boards and integrated circuits. Besides the inorganic components of these plating solutions (copper ions, sulfuric acid and small amounts of chloride ions) the baths contain one or more organic additives (brighteners, suppressors and levelers). In the proper concentrations, these organic additives give a bright, smooth deposit with excellent mechanical and electrical properties.

Analyses of plating bath additives are described by Tench and coworkers in U.S. Pat. No. 4,132,605, and Fisher in U.S. Pat. Nos. 4,917,774 and 4,917,777. These methods were devised to measure the brightener concentration in a bath containing a suppressor and inorganic components only. These methods cannot measure the presence of a leveler component in a plating bath containing brightener and suppressor.

The electrochemical methods for plating bath analysis described by Tench et al. and Fisher rely on the fact that the brightener and suppressor work in opposition to one another with respect to their effect on the potential of an object being plated. Suppressors, as their name implies, increase the overpotential for plating and thus suppress the plating rate for any given electrical energy input to the bath. In the presence of suppressors, brighteners lower the plating overpotential and cause the plating rate to increase for any given input of electrical energy to the plating bath. Suppressors cause an abrupt suppression of the plating rate at very low concentrations, on the order of 50 parts per million or less. Above that threshold level the plating overpotential changes very little, if at all. Suppressor concentrations are usually kept in the range of several hundreds to several thousand parts per million to ensure that the suppressor concentration is always well above the threshold value.

U.S. Pat. Nos. 4,917,774 and 4,917,777 essentially describe a stepped potential method where a three electrode cell is employed. The electrodes are 1) a working electrode, 2) a counter electrode, and 3) a reference electrode, which are all immersed in the plating solution to be analyzed. The working electrode is a noble metal such as platinum in the form of a rotating disc. The disc is sealed at one end of a Kel F rod and is rotated during the analysis to ensure that uniform hydrodynamic conditions prevail. The potential of the working electrode is controlled by input from a potentiostat slaved to a computer. For any working potential required, the computer will direct the potentiostat to set the potential difference between the counter electrode and the reference electrode to give the desired potential at the working electrode. The computer and potentiostat can be embodied in a single unit such as the Electroposit™ Bath Analyzer, (Shipley Company, Marlborough, Mass. and S-Sytems, Norwood, Mass.). The potential of a working electrode is held at various potentials in a plating solution to clean, equilibrate, plate and strip the plated deposit from the electrode. A measurement of the initial current flowing during the plating step is directly related to the brightener concentration in the plating solution. When using the Electroposit™ Bath Analyzer, the initial plating current is displayed as Total Brightener Analysis Units ("TBA") units, hereinafter referred to as TBA analysis.

Levelers often are present in plating baths. Like suppressors, levelers cause a reduction of plating rate for any given electrical energy input to the plating bath. Unlike suppressors, whose effect is general in nature, levelers cause a localized depression in plating rate. They act under mass transfer control to suppress the plating rate by adsorbing at locally higher potential regions of the article being plated. The above described electrochemical methods cannot be used when levelers are present in the bath. This is due to the leveler's suppressing effect on the plating rate, which varies with its concentration in the bath. To properly analyze for brightener when leveler is present the leveler concentration must already be known. The techniques described above provide no solution for overcoming the confounding effect of the leveler on the brightener, and therefore cannot be used when these two additives coexist in a plating bath.

U.S. Pat. No. 5,223,118 to Sonnenberg et al. describes an analysis method that measures both brightener and leveler coexisting with suppressor in a plating solution. In this method the brightener concentration is first determined by the TBA method and, if necessary, adjusted by external addition to a value that gives maximum sensitivity for analysis of leveler. The method then uses a freshly prepared copper coated electrode to monitor the energy input with time to the electrode while plating at an applied current held at a constant value. Such copper coated electrode is prepared by first plating copper from a separate copper electroplating solution free of organic additive on an electrode of a different metal. The electrode typically is platinum. The slope of the resulting energy-time plot is used to quantitatively determine the leveler concentration.

To repeat the analysis method all of the copper is removed from the platinum by a nitric etch, which also removes adsorbed bath components from the electrode. The copper also may be removed with an anodic potential/current. Nevertheless, a nitric acid etch is still needed to remove any adsorbed species on the electrode. The nitric acid etch and the electrochemical stripping of copper from the electrode cleans the electrode of varying amounts of metal oxide and metal chloride on the electrode surface. Such oxides on the electrode surface alter the plating potential and steps for forming a copper film on the electrode, which in turn affects the adsorption behavior of organic additives. Such surface inconsistencies compromise the reproducibility of measuring organic bath additives and increase the error in determining concentrations of the organic additives.

While the Fisher and Sonnenberg patents are improvements over the Tench methods for analyzing organic additives for plating baths, workers in the art are always seeking improved analytical methods that provide measurements that are more reproducible, thus reducing the amount of error. Reducing error in the measurement of organic additives of electroplating baths is highly desirable in the electroplating industry. An undesirable decline or increase in organic additives during electroplating processes may result in a defective end product, thus increasing the cost and decreasing the efficiency of the manufacture of articles prepared by electroplating. Many organic additives in electroplating baths, such as brighteners and levelers, are employed in relatively low concentrations. Accordingly, changes in bath concentrations of such organic additives have a pronounced detrimental affect on the quality of the final product.

Accordingly, there is a continuing need for the analysis of brightener and leveler concentrations in plating baths that works over a wide range of brightener concentrations, is simple to perform and does not require the addition of other components to the bath for the procedure to be performed and provides reproducible measurements.

SUMMARY OF INVENTION

The present invention is directed to a method for determining the quantity of brightener and leveler in a metal plating bath that includes: a) obtaining a plurality of plating bath samples where each bath sample has a known and different quantity of the brightener and the leveler, but where the quantity of each in each bath sample differs from the quantity in the other bath samples; b) for each bath sample, providing a counter electrode, a cleaned working electrode and a reference electrode and carrying out a predetermined sequence of steps that includes: 1. cleaning and conditioning the working electrode; 2. equilibrating the working electrode without energy input to adsorb brightener and measuring the energy output; 3. plating metal ions on the working electrode with energy input for a time sufficient to measure initial plating energy output; and 4. continuing to plate metal ions for a time sufficient to measure the change in energy output with time; c) for each bath sample, correlating the quantity of brightener with the output value obtained in step 2; d) for each bath sample, correlating the quantity of brightener with the initial energy output value obtained in step 3; e) for each bath sample, correlating the ratio of brightener to leveler with the change in energy output with the time value obtained in step 4; f) obtaining a plating bath sample having an unknown quantity of brightener and leveler, and performing the predetermined sequence of steps; and g) choosing from the correlations in steps c, d and e, a quantity of brightener and the ratio of brightener to leveler which corresponds to the energy output recorded for the bath sample with the unknown quantity of brightener and leveler.

In another embodiment, the present invention is directed to a method for determining the quantity of one or more brighteners in a metal plating bath that includes: a) obtaining a plurality of plating bath samples, each having a known quantity of the brightener, but where the quantity of the brightener in each bath sample differs from the quantity in the other bath samples; b) for each bath sample, providing a counter electrode, a cleaned and conditioned working electrode and a reference electrode, immersing the electrodes in the bath sample, and equilibrating the working electrode without energy input to adsorb brightener for a time ranging between five seconds and twenty minutes while monitoring the change in potential of the working electrode with time; c) for each bath sample, correlating the quantity of brightener with the value of potential obtained in step b; d) obtaining a plating bath sample having an unknown quantity of brightener, and performing step b for the plating bath sample; and e) choosing from the correlation in step c) a quantity of brightener which corresponds to the equilibrated working electrode potential for the bath sample with the unknown quantity of brightener.

In a further embodiment, the present invention is directed to a method of determining a quantity of leveler that includes: a) a plurality of bath samples is provided where each bath sample has a known and different quantity of brightener and leveler, where the quantity of leveler in each bath sample differs from the quantity in the other bath samples are the quantity of brightener in each bath sample is the same, only the quantity of leveler varies; b) providing a cleaned and conditioned working electrode and a reference electrode and carrying out a predetermined sequence of steps, the steps include: 1. cleaning and oxidizing the surface of the working electrode at a fixed potential for a period of time; 2. conditioning the working electrode at a varying potential for a period of time; 3. equilibrating the working electrode to adsorb brightener by equilibrating without energy input for a time until the change in energy output with time is minimal; 4. plating metal ions on the working electrode with energy input for a time sufficient to measure initial plating energy output; 5. optionally continuing to plate metal ions for a time sufficient to measure the change in energy output with time; 6. stripping at a potential and for a period of time sufficient to remove the metal ions plated in steps 4 and 5; c) for each bath sample, correlating the quantity of leveler with the energy output value obtained in step 4 or 5; d) obtaining a plating bath sample having an unknown quantity of leveler; e) diluting the bath sample having an unknown quantity of leveler with a leveler-free composition including a fixed concentration of brightener and performing the predetermined sequence of steps; f) choosing from the correlation in step c) a quantity of leveler which corresponds to the energy outputs recorded for the bath sample with the unknown quantity of leveler.

Unexpectedly, the cleaning process and the conditioning step of the present invention improves the reproducibility of a working electrode's performance during analysis of plating bath organic additives, thus providing a more reliable method of determining organic bath additives. Accordingly, workers may maintain organic bath additives at optimum levels, thus providing a more efficient means of manufacturing articles prepared by metal plating.

DETAILED DESCRIPTION OF THE INVENTION

Figure 1:
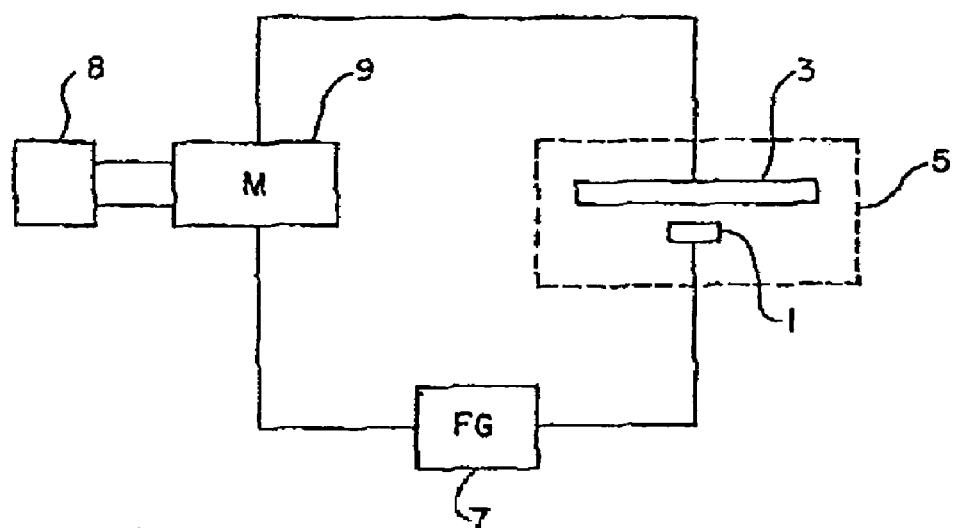
FIG. 1 is a schematic wiring diagram of a device according to an embodiment of the invention.

The following abbreviations shall have the following meanings unless the text clearly indicates otherwise: ° C.=degrees Centigrade; g/L=grams per liter; cm=centimeter; mA=milliamperes; mA/cm$^2$=milliamperes per square centimeter; mL=milliliter; mL/L=milliliters per liter; V=volts; ppm=parts per million; ppb=parts per billion.

As used throughout this specification, the term "plating" refers to metal electroplating, unless the context clearly indicates otherwise. "Deposition" and "plating" are used interchangeably throughout this specification. "Halo" refers to fluoro, chloro, bromo, and iodo. Likewise, "halide" refers to fluoride, chloride, bromide and iodide. "Alkyl" includes straight chain, branched and cyclic alkyl groups. "Brightener" refers to an organic additive that increases the plating rate of the electroplating bath. The terms "brightener" and "accelerator" are used interchangeably throughout this specification. "Leveler" refers to an organic compound that is capable of providing a substantially planar metal layer during plating. "Energy output" refers to any energy output and includes energy flow, energy throughput and current. "Energy input" refers to any energy input and includes potential energy, cell potential, electrode potential and reductive potential.

All percentages and ratios are by weight unless otherwise indicated. All ranges are inclusive and combinable in any order.

The subject invention provides a method for determining the quantity of organic bath additives such as brighteners and levelers coexisting in a plating solution. Also, the present method provides a method for determining the quantities of both brightener and leveler that is more accurate than conventional methods. More importantly, the present invention provides for a method for determining the quantities of both brightener and leveler with improved reproducibility in contrast to conventional methods.

Unexpectedly, the cleaning process and the conditioning step of the present invention improves the reproducibility of working electrode performance such that the working electrode may be employed in a method for determining the amount of organic bath additives such that the measurements are more reliable than if the cleaning process and the conditioning step were not employed. The cleaning and conditioning step reduces the potential for error in measuring organic bath additives such as brighteners and levelers. Accordingly, workers in the art may now obtain measurements of organic bath additive quantities that they may rely on to replenish working plating baths with organic additives to return the levels of the organic additives to optimum operating levels.

The conditioning step is subsequent to a cleaning process for a working electrode. Cleaning a working electrode may involve an acid etch, such as a nitric acid etch, or by applying an anodic electrical potential. Anodic cleaning ranges from 0.01 second to 5 minutes, preferably from 1 second to 2 minutes. The acid etch removes both plated metal and any adsorbed organic species from the working electrode. If an anodic potential is applied, an acidic solution is still employed to remove any adsorbed species on the working electrode. The electrochemical cleaning process leaves the working electrode with varying degrees of metal oxide and metal chloride. The metal oxide and metal chloride formed on the surface of the working electrode alters the plating potential for a metal that is to be plated on the electrode. When the plating potential for forming a metal film on the working electrode changes, the ability to adsorb organic additives on the electrode also changes, thus compromising reproducibility of measuring bath organic additives. The acid etch cleaning step counter acts the detrimental effects of the metal oxide and metal chloride on the surface of the working electrode.

Anodic potential is a potential where metal ions of a plating bath do not deposit on a working potential. In contrast a cathodic potential is a potential where the metal ions from the bath deposit on the working electrode. Such potentials may vary depending on the metal to be plated. Minor experimentation may be performed to determine such potentials for a given working electrode and bath. Many procedures are well known to those of skill in the art.

The conditioning step is performed in a bath that does not contain organic additives but only inorganic components of plating baths. Such inorganic baths may include a metal salt of the metal that is to be plated, optionally one or more inorganic acids, and, optionally, a source of chloride ions. Such baths typically are aqueous. The conditioning step begins with a cycle that includes applying a potential that is anodic such that metal is not plated on the working electrode, followed by a cathodic sweep where a thin metal film is plated on the working electrode and then an anodic sweep is applied to the working electrode to strip the metal from the working electrode. Current densities may range from 1.0 mA/cm$^2$ to 100 mA/cm$^2$, preferably from 10 mA/cm$^2$ to 80 mA/cm$^2$, more preferably from 25 mA/cm$^2$ to 65 mA/cm$^2$. The conditioning step may range from 0.05 seconds to 5 minutes, preferably from 5 seconds to 3 minutes, more preferably from 10 seconds to 1 minute. For example, the conditioning step may end with a thin layer (5 to 500 microinches) of the metal in the additive free plating bath galvanically plated onto the surface of the electrode at a current density of 30 mA/cm$^2$.

After the working electrode is conditioned, the working electrode is equilibrated in a bath containing organic additives as well as the inorganic components. The equilibration step allows the adsorption of organic additives, such as suppressors and brighteners, for a time necessary to determine the concentration of the brighteners. The cell is typically left at open circuit (no applied potential) during the equilibration step, and the resulting change in potential vs. time is plotted. The equilibration step may last long enough such that the concentration of the brighteners may be determined or until the equilibration potential becomes stable (i.e., change in potential is minimal). The equilibration potential may be correlated to brightener concentration. Equilibration ranges from 0.01 seconds to 20 minutes, preferably from 5 seconds to 10 minutes. An optional anodic pulse step may be used after equilibration to increase sensitivity of the working electrode. The anodic pulse step may be from 0.05 seconds to 10 minutes.

After the equilibration step, metal is plated on the working electrode first to measure brightener concentrations, and then the rate of change of energy output from the system is recorded in order to determine leveler concentration. As metal ions are being deposited on the working electrode the metal ions may be combined with or bound to levelers, brighteners, chloride ions, water or wetting agents present in the bath. The initial potential recorded may be able to be correlated to a measure of brightener concentration.

When the energy output is plotted versus time, the slope of the line indicates the ratio of brightener to leveler present in the bath. Slopes may vary depending on the absolute concentration of brightener. Once the quantity of brightener is determined from the previous steps, additional brightener may be added in the sample such that the amount of brightener more closely approximates the actual value of brightener in the standards. Once this is done the ratio of brightener to leveler more accurately reflects the absolute amount of leveler. The sensitivity of the process of the present invention allows for the determination of organic additive concentrations down to 1 ppb.

As the plating process continues changes in potential also may be correlated to the ratio of brightener to leveler. This is done by plotting the changes in voltage over time for various standard concentrations of leveler when the brightener concentration is held constant. The slope of the lines may be correlated to the ratio of brightener to leveler in the bath, and is used to determine the quantity of leveler present in the bath.

After the process of measuring the quantity of organic additives is complete, the working electrode is cleaned and conditioned and the process may be repeated with another unknown.

The specific potential ranges for the conditioning step may vary depending on the type of metal to be plated from a bath. Potentials for plating and stripping many metals from a working electrode are known in the art, however, if such potentials for a given metal are unknown, they may be determined. This can be performed, for example, by a voltammetric sweep of an electrode in a solution containing metal ions, plating the metal ions on the electrode, and then noting the potential at which anodic stripping current occurs.

A wide variety of electroplating baths may be analyzed according to the present invention to determine the quantity of brightener and leveler. Suitable electroplating baths include, but are not limited to, copper, nickel, chromium, zinc, tin, lead, gold, silver, and cadmium electroplating baths. The methods of the present invention are preferably employed in measuring organic additives for copper plating baths.

Working electrodes include any that provide a uniform current density and controlled agitation. Suitable working electrodes include, but are not limited to: platinum, copper, nickel, glassy carbon, palladium, rhodium, ruthenium, chromium, zinc, tin, gold, silver, lead, cadmium, graphite, mercury and stainless steel. Preferably, the working electrode is a noble metal, more preferably platinum or gold, and even more preferably gold. The working electrode typically has a flat, polished surface, small diameter and may be mounted flush with the end of a Kel-F cylinder. To establish relative motion between the working electrode and the bath, a motor may be used to rotate the working electrode to which contact is made by slip brushes. Thus, it is further preferred that the working electrode is a rotating disk electrode ("RDE"). A small diameter disk is preferred since a larger diameter may result in poor sensitivity due to non-uniform current density across the diameter. The working electrode used in the brightener quantitative determination step and in the leveler quantitative determination step may be the same or different. Preferably both are gold. The reference electrode is conventionally, a saturated Calomel reference electrode ("SCE") or a standard hydrogen electrode ("SHE"). The counter electrode, for example, may be an noble metal, noble metal oxide, or noble metal alloy such as gold, platinum, iridium oxide coated titanium, platinum-ruthenium or may be a soluble anode composed of the same metal that is present in the electrolyte bath such as a soluble copper anode for use with a copper electrolyte bath.

FIG. 1 is a schematic wiring diagram showing a device for determining the quantity of brightener according to the present invention. A working electrode 1 and a counter electrode 3 are immersed in a bath in cell 5. The counter electrode is selected and designed so as not to be easily polarized in the particular bath being evaluated. This is accomplished, in part, by making the counter electrode large relative to the working electrode and by placing it close to the working electrode.

A function generator 7 sweeps the working electrode 1 through a voltage versus time cycle at a specific rate while a coulometer 9 measures the coulombs (amp-seconds) flowing between the counter electrode 3 and the working electrode 1 during the metal stripping portion of the voltammetric cycle. The coulometer may be an ammeter whose output can be fed into a recorder for determining the coulombs utilized during the stripping portion of the cycle, or the output can go directly into a microprocessor or computer 8 for direct correlation and comparison of the coulombs utilized.

Figure 2:
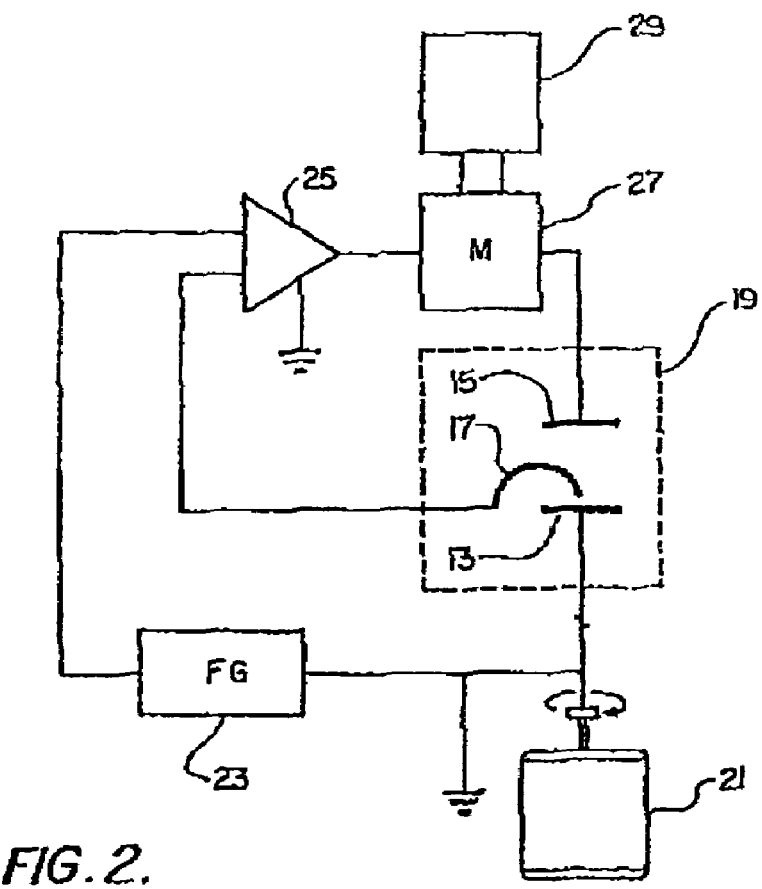
FIG. 2 is a schematic wiring diagram of a device according to another embodiment of the invention.

FIG. 2 shows the schematic wiring diagram for a more elaborate device for determining the quantity of brightener. Three electrodes, a working electrode 13, a counter electrode 15, and a reference electrode 17, are immersed in a bath in cell 19. To establish relative motion between the working electrode 13 and the bath, a motor 21 is used to rotate the working electrode 13 to which contact is made by slip brushes.

In one embodiment, the working electrode 13 is gold and the counter electrode 15 is iridium oxide coated titanium, although any conductive material, which is inert in the particular bath, can be used. The rotatable working electrode 13 has a flat, polished surface, 0.13 cm$^2$ in area, mounted flush with the end of a 1.27 cm diameter Kel-F cylinder. The reference electrode 17 is a saturated calomel reference electrode ("SCE"). A function generator 23 and an electronic potentiostat 25 are used to control the potential relative to the reference electrode 17. A digital coulometer 27 measures the coulombs flowing during the stripping portion of the voltammetric cycle.

A microprocessor or computer 29 can be coupled to the digital coulometer to compare the measured coulombs with a previously established correlation. The microprocessor or computer 8, 29, shown in FIGS. 1 and 2, can be coupled to the circuit so that they are triggered either manually or by a suitable signal from the function generator 7, 23, or from the working electrode 1, 13.

To achieve maximum sensitivity, there must be sufficient relative motion between the working electrode and the bath to maintain a uniform supply of plating ingredients at the electrode surface. Without such motion, the metal ions become depleted at the surface of the electrode. In the embodiment shown in FIG. 2, the working electrode 13 is rotated by motor 21 to obtain controlled relative motion between it and the plating bath. Other means of obtaining relative motion can be used, such as a pump for moving the bath across the face of the electrode.

Figure 3:
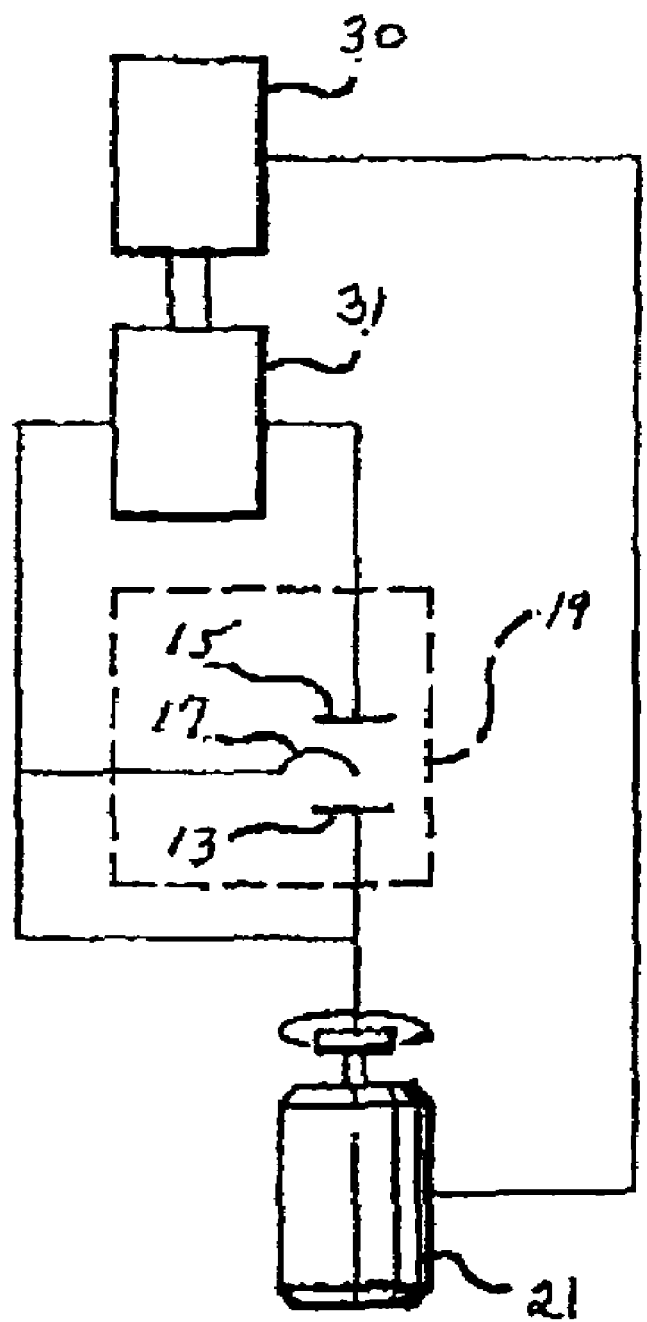
FIG. 3 is a schematic wiring diagram of a device according to a third embodiment of the invention.

FIG. 3 is a schematic wiring diagram showing a device suitable for the determination of quantity of leveler according to the present invention. Three electrodes, a working electrode 13, a counter electrode 15, and a reference electrode 17, are immersed in a bath in cell 19. To establish relative motion between the working electrode 13 and the bath, a motor 21 is used to rotate the working electrode 13 to which contact is made by slip brushes. A computer 30 is used to control an electronic potentiostat 31, which controls the energy input between the working electrode and counter electrode relative to the reference electrode. Using a suitable program, the energy input sequences of the present invention may be applied to the working electrode. The output of the device also may be plotted on a recorder to graphically display the changes in energy output versus time for each step.

In addition to copper, the methods may be used to control other metal electroplating baths such as nickel, chromium, zinc, tin, gold, silver, lead, cadmium and solder. The working electrode may be selected or initially plated to match the metal in the plating bath in order to maximize adsorption of the respective brighteners used in the baths.

While the present invention may be used with a wide variety of plating baths, the following illustration is with respect to a copper electroplating bath. A typical copper electroplating bath useful for the practice of this invention has a composition as follows:

| Component | Amount |
| --- | --- |
| Copper ions | 2.5 to 40.0 g/l |
| Sulfuric acid (added) | 0 to 450 g/l |
| Chloride ions | 20 to 100 ppm |
| Organic additives | As needed |
| Water | To 1 liter |

The plating solutions are used in the conventional manner, with operating temperatures from 10° and 40° C., and controlled solution agitation.

The method of determining the quantity of leveler typically begins with a cleaning step to clean the working electrode. The working electrode is typically cleaned chemically by treating with nitric acid followed by rinsing with deionized water. The chemically cleaned working electrode is immersed in the bath to be analyzed along with a counter electrode. Once immersed in the bath, the working electrode is then cleaned and oxidized at a fixed potential for a period of time. Such potentiometric cleaning may be carried out at 100 mA/cm$^2$ for a time sufficient to clean the electrode or until the voltage reaches 1.6 volts. Alternatively, the cleaning may be carried out at 1.6 volts for a period of time such as up to 10 seconds.

After cleaning the working electrode is conditioned. The working electrode is placed in a bath containing inorganic components only. Such components include copper ions, sulfuric acid, chloride ions and water. A potential sweep is applied in the anodic range, cathodic range and back to an anodic range. For example, an anodic potential of 1.6 volts is applied to the disk, then the potential is swept cathodic by lowering the potential to −0.25 volts at, say 50 mV/sec, followed by sweeping the potential to an anodic level of 1.6 volts at the same sweep rate.

Optionally, the third step is to plate a thin layer of copper, 5 to 500 microinches, on the disk by placing the disk in an electroplating bath solution for 10 to 300 seconds at a plating current of from 1 to 100 mA/cm$^2$. The solution may be a standard solution containing only the inorganic chemicals or an actual bath.

Brighteners and levelers used in conjunction with the present invention include any sulfonated sulfur-containing compounds, which are known and used in the electroplating art. Suitable brighteners useful in the practice of the invention contain the group $HSO_3—R_1—S—$, where $R_1$ may be an alkyl or aryl group, and are illustrated by the following structural formulas: $HO_3S—R_1—SH$, $HO_3S—R_1—S—S—R_1—SO_3H$ (where $R_1=C_1-C_6$ alkyl) and $HO_3S—Ar—S—S—Ar—SO_3H$ (where Ar=phenyl or naphthyl). Typical of such compounds are those disclosed in U.S. Pat. Nos. 3,770,598, 4,374,709, 4,376,685, 4,555,315 and 4,673,469, all incorporated herein by reference.

Levelers that may be added to the bath included those that contain a $N—R_1—S$ group, where $R_1$ may be an alkyl or aryl group, and are illustrated by compounds disclosed in U.S. Pat. Nos. 4,376,685, 4,555,315, and 3,770,598, all incorporated herein by reference. Other suitable levelers include reaction products of amines such as imidazole with epoxides such as epichlorohydrin.

In addition to the organic components identified above, as is known in the art, other organic additives may be used in the plating bath such as surfactants, wetting agents and carriers.

The electrode may be equilibrated by not applying current to the electrodes (open circuit potential or "OCP") and allowing the disk electrode to adsorb brightener for a period of time typically ranging between 5 seconds to 20 minutes, or until the equilibration potential becomes stable (i.e. change in potential with time is minimal). Optionally, an additional anodic pulse may be used after the equilibration step. The anodic pulse is carried out at 0.01 volts to 1.6 volts for a period of time ranging from 0.001 to 10 minutes.

In the next step, copper plating is initiated by plating at a current density from 1 to 100 mA/cm$^2$ for 0.001 second to 180 seconds. During this time, copper ions are deposited on the electrode. These ions may be combined with or bound to leveler, brightener, chloride ions, water and/or wetting agents present in the bath sample. The initial potential reading, upon initiation of plating, is directly related to the leveler concentration. The initial potential may be correlated to the concentration of leveler.

Optionally, the plating may be continued for a period of time to measure the change in energy output with time. As the plating process continues, changes in energy output can also be correlated to the concentration of leveler. This step of continued plating may be for a period of time ranging between 1 second to 10 minutes. The slope of plots of changes in energy output over time for various standard concentrations of leveler when the brightener is held constant can be correlated to the ratio of brightener to leveler in the bath sample, and is used to determine quantity of leveler present in the bath sample.

After the metal ions have been plated or deposited, they are stripped or removed from the electrode. Such stripping is at a potential and for a period of time sufficient to substantially remove and preferably remove the metal ions deposited during the initial and optionally continued plating steps. The period of time of such stripping is dependent upon the thickness of the metal deposited. The potential at which such metal is stripped is dependent upon the particular metal deposited. For example, when the deposit is copper, it may be stripped at a potential of +0.2 V for 0.5 to 5 seconds.

In another embodiment, a plurality of plating bath samples where each bath sample has a known and different quantity of brightener and leveler, wherein the quantity of leveler in each bath sample differs from the quantity in the other bath samples are prepared to provide a standard curve. The quantity of brightener in each bath sample is the same, only the quantity of leveler varies.

In the first step of this alternative procedure, a counter electrode, a cleaned and conditioned working electrode and a reference electrode are provided for each bath sample, and a predetermined sequence of steps are performed, the steps including: 1. cleaning and oxidizing the surface of the working electrode at a fixed potential for a period of time;

2. conditioning the working electrode for a period of time; 3. equilibrating the working electrode to adsorb brightener without energy input for a time until the change in energy output with time is minimal; 4. plating metal ions on the working electrode with energy input for a time sufficient to measure initial plating energy output; and 5. optionally continuing to plate metal ions for a time sufficient to measure the change in energy output with time. The quantity of leveler is correlated with the energy output value obtained in step 4 or 5. This provides a standard curve rather than the usual family of curves that are obtained by the methods described above.

A plating bath sample having an unknown quantity of leveler is diluted with a leveler-free composition including a fixed concentration of brightener. The fixed concentration of brightener is that concentration of brightener used in the plating bath sample. Preferably, the leveler-free composition further includes the same components used in the plating bath sample being analyzed, except that leveler is not present. Thus, it is further preferred that the leveler-free composition include the same metal as in the electroplating bath and suppressor. Preferably, the sample of the bath having an unknown quantity of leveler is diluted 5 to 1, and more preferably 10 to 1 with the leveler-free composition. The above predetermined sequence of steps then are performed. The energy output recorded is then compared to the calibration curve (correlation) to quantify of leveler.

Thus, the present invention further provides a method for determining the quantity of leveler in an electroplating bath sample that includes the steps of: a) obtaining a plurality of plating bath samples where each bath sample has a known and different quantity of brightener and leveler, where the quantity of leveler in each bath sample differs from the quantity in the other bath samples; b) for each bath sample, providing a counter electrode, a cleaned and conditioned working electrode and a reference electrode, and carrying out a predetermined sequence of steps comprising: 1. cleaning and oxidizing the surface of the working electrode at a fixed potential for a period of time; 2. conditioning the electrode for a period of time; 3. equilibrating the working electrode to adsorb brightener without energy input for a time until the change in energy output with time is minimal and equilibrating for a set time at a fixed potential; 4. plating metal ions on the working electrode with energy input for a time sufficient to measure initial plating energy output; and 5. optionally continuing to plate metal ions for a time sufficient to measure the change in energy output with time; 6. stripping at a potential and for a period of time sufficient to remove the metal ions plated in steps 4 and 5; c) for each bath sample, correlating the quantity of leveler with the energy output value obtained in step 4 or 5; d) obtaining a plating bath sample having an unknown quantity of leveler; e) diluting the bath sample having an unknown quantity of leveler with a leveler-free composition comprising a fixed concentration of brightener and placing the electrodes in the bath and performing the predetermined sequence of steps; f) choosing from the correlation in step c) a quantity of leveler which corresponds to the energy outputs recorded for the bath sample with the unknown quantity of leveler.

The above methods may be performed at a range of temperatures. The analysis of the bath sample containing the unknown amount of leveler should be performed at the same temperature as the calibration curve samples or family of calibration curve samples. A concentration of brightener of 2 ppm or greater suffices to provide sufficient accuracy for analysis of the leveler, preferably from 2 to 25 ppm.

The following example is presented to illustrate further various aspects of the present invention, but are not intended to limit the scope of the invention in any aspect.

EXAMPLE 1

Comparison of Reproducibility of Results with and Without Nitric Etch

The platinum electrode was conditioned by placing the electrode in a copper electroplating bath sample containing no organic additives and performing a potential sweep. The initial potential was 1.6 V (all potentials are vs. SCE), and was swept to −0.2 V at a rate of 50 mV/sec. The potential ws then swept back to 1.6 V at the same sweep rate. The platinum electrode was a flat disk with a diameter of 4 mm. The electrode was rotated throughout the analysis at 3600 rpm. The apparatus employed is schematically represented in FIG. 3. A three electrode cell was employed with an iridium oxide coated titanium counter electrode, and a saturated calomel reference electrode. The inorganic bath components for conditioning the platinum working electrode are in Table I below:

TABLE I

| Component | Quantity |
| --- | --- |
| Copper sulfate pentahydrate | 80.0 g/L |
| Sulfuric acid | 225 g/L |
| Chloride ions | 50 mg/L |
| Water | To 1 liter |

After conditioning, a thin layer of copper of 10 microinches was plated on the disk electrode. The disk was plated in the solution described in Table I above. The copper was plated galvanostatically at a constant current of 30 asf. Plating of copper on the disk was performed for 180 seconds. The copper film formed on the platinum working electrode eliminated problems associated with nucleation of metal on the electrode during analysis.

The electrode was then placed in a bath sample containing 5 mL/L of Shipley EP 1100B-1 brightener, and 15 mL/L of Copper Gleam ST 901® carrier solution. The energy output was monitored with a Shipley bath analyzer with no energy input for 10 minutes. The energy output vs. time was plotted on the screen. The energy output changes with respect to the amount of brightener that was adsorbed onto the surface of the electrode. The slope of the line was then calculated in the change in potential from 180 seconds to 500 seconds in the plot.

Following the equilibration, copper was plated on the electrode for 60 seconds, with the energy output being monitored at a constant cathodic current of 30 asf applied to the working electrode.

Prior to each measurement, a nitric acid etch was either performed or not to determine the reproducibility of the process, the average slope of each is presented in Table II.

TABLE II

| Sample Number | Nitric Etch | Avg slope | Std Deviation |
| --- | --- | --- | --- |
| 10-12 | Yes | 0.0866 | 0.015 |
| 1-3 | No | 0.0733 | 0.032 |

From the above example, the nitric etch generates an average slope with a smaller standard deviation, and therefore, better reproducibility.

What is claimed is:

1. A method for determining the quantity of both brightener and leveler in a metal plating bath comprising:
   a) obtaining a plurality of plating bath samples where each bath sample has a known and different quantity of the brightener and the leveler, but where the quantity of each in each bath sample differs from the quantity in the other bath samples;
   b) for each bath sample, providing a counter electrode, a cleaned working electrode and a reference electrode and carrying out a predetermined sequence of steps comprising:
      1. conditioning the working electrode by applying a potential to the working electrode that is anodic followed by a cathodic potential and then an anodic potential and then etching the working electrode with nitric acid;
      2. equilibrating the working electrode without energy input to adsorb brightener for a time until the change in energy output with time is minimal and measuring the energy output;
      3. plating metal ions on the working electrode with energy input for a time sufficient to measure initial plating energy output; and
      4. continuing to plate metal ions for a time sufficient to measure the change in energy output with time;
   c) for each bath sample, correlating the quantity of brightener with the energy output value obtained in step 2;
   d) for each bath sample, correlating the quantity of brightener with the initial energy output value obtained in step 3;
   e) for each bath sample, correlating the ratio of brightener to leveler with the change in energy output with the time value obtained in step 4;
   f) obtaining a plating bath sample having an unknown quantity of brightener and leveler, placing the electrodes in the bath sample and performing the predetermined sequence of steps; and
   g) choosing from the correlations in steps c, d and e, a quantity of brightener and the ratio of brightener to leveler which corresponds to the energy output recorded for the bath sample with the unknown quantity of brightener and leveler.

2. The method of claim 1, wherein a current density for the conditioning ranges from 1.0 A/cm$^2$ to 100 A/cm$^2$.

3. The method of claim 1, wherein the conditioning step ranges from 0.5 seconds to 5 minutes.

4. The method of claim 1, wherein the working electrode is conditioned in a bath sample free of organic additives.

5. The method of claim 1, wherein the working electrode comprises a noble metal on a non-noble metal.

6. The method of claim 1, further applying an anodic potential for a time after equilibrating the working electrode.

7. A method for determining a quantity of one or more brighteners in a metal plating bath comprising:
   a) obtaining a plurality of plating bath samples, each having a known quantity of the brightener, but where the quantity of the brightener in each bath sample differs from the quantity in the other bath samples;
   b) for each bath sample, providing a counter electrode, a cleaned working electrode and a reference electrode, conditioning the working electrode by applying a potential to the working electrode which is anodic followed by a cathodic potential followed by an anodic potential and then etching the working electrode with nitric acid, immersing the electrodes in the bath sample, and equilibrating the working electrode without energy input to adsorb brightener for a time ranging between five seconds and twenty minutes until the change in the potential of the working electrode with time is minimal and measuring the value of the potential;
   c) for each bath sample, correlating the quantity of brightener with the value of potential obtained in step b;
   d) obtaining a plating bath sample having an unknown quantity of brightener and performing step b for the plating bath sample; and
   e) choosing from the correlation in step c a quantity of brightener which corresponds to the equilibrated working electrode potential for the bath sample with the unknown quantity of brightener.

8. A method for determining the quantity of leveler in an electroplating bath comprising the steps of:
   a) obtaining a plurality of plating bath samples where each bath sample has a known and different quantity of brightener and leveler, wherein the quantity of leveler in each bath sample differs from the quantity in the other bath samples;
   b) for each bath sample, providing a counter electrode, a working electrode and a reference electrode and carrying out a predetermined sequence of steps comprising:
      1. cleaning and oxidizing the surface of the working electrode at a fixed potential for a period of time;
      2. conditioning the working electrode for a period of time by applying a potential to the working electrode which is anodic followed by a cathodic potential followed by an anodic potential and then etching the working electrode with nitric acid;
      3. equilibrating the working electrode to adsorb brightener by equilibrating without energy input for a time until the change in energy output with time is minimal;
      4. plating metal ions on the working electrode with energy input for a time sufficient to measure initial plating energy output;
      5. optionally continuing to plate metal ions for a time sufficient to measure the change in energy output with time; and
      6. stripping at a potential and for a period of time sufficient to remove the metal ions plated in steps 4 and 5;
   c) for each bath sample, correlating the quantity of leveler with the energy output value obtained in step 4 or 5;
   d) obtaining a plating bath sample having an unknown quantity of leveler;
   e) diluting the bath sample having an unknown quantity of leveler with a leveler-free composition comprising a fixed concentration of brightener and performing the predetermined sequence of steps;
   f) choosing from the correlation in step c), a quantity of leveler which corresponds to the energy outputs recorded for the bath sample with the unknown quantity of leveler.

* * * * *